United States Patent [19]

Sabato

[11] 4,262,425
[45] Apr. 21, 1981

[54] SELF-ADJUSTING INSPECTION APPARATUS

[75] Inventor: Joseph G. Sabato, Fairfield, Ohio

[73] Assignee: General Electric Company, Cincinnati, Ohio

[21] Appl. No.: 159,080

[22] Filed: Jun. 13, 1980

[51] Int. Cl.³ .............................................. G01B 7/12
[52] U.S. Cl. ................................ 33/178 R; 33/149 J; 33/178 B; 33/178 E
[58] Field of Search ............. 33/178 R, 178 E, 169 C, 33/143 R, 143 L, 174 E, 149 R, 147 K, 149 J, 172 D, 178 B, 174 L

[56] References Cited

U.S. PATENT DOCUMENTS

| 2,454,159 | 11/1948 | Graves | 33/178 B |
|---|---|---|---|
| 2,758,383 | 8/1956 | Breit | 33/178 R |
| 2,770,773 | 11/1956 | Cooley | 324/37 |
| 2,801,474 | 8/1957 | Field et al. | 33/178 R |

*Primary Examiner*—Willis Little

*Attorney, Agent, or Firm*—Carl L. Silverman; Derek P. Lawrence

[57] ABSTRACT

The inspection apparatus self-adjusts for inspecting bolt-holes of a predetermined size range between a minimum inspection diameter and a maximum inspection diameter. A probe shaft is coupled through a ramp portion to a pear-shaped probe head. The probe head includes a sensor element at the perimeter thereof. An axial slot extends through the shaft and the probe head, dividing the probe head into two probe head sections. A first spring couples the probe head sections and normally urges the sections away from each other and toward the maximum inspection diameter. A cup is slidably positioned around the ramp portion such that, as the cup slides along the ramp portion toward the probe head, the two probe head sections are urged together and the minimum inspection diameter is approached. A second spring is positioned about the shaft to normally urge the cup to an extreme position along the ramp portion, resulting in the minimum inspection diameter.

10 Claims, 6 Drawing Figures

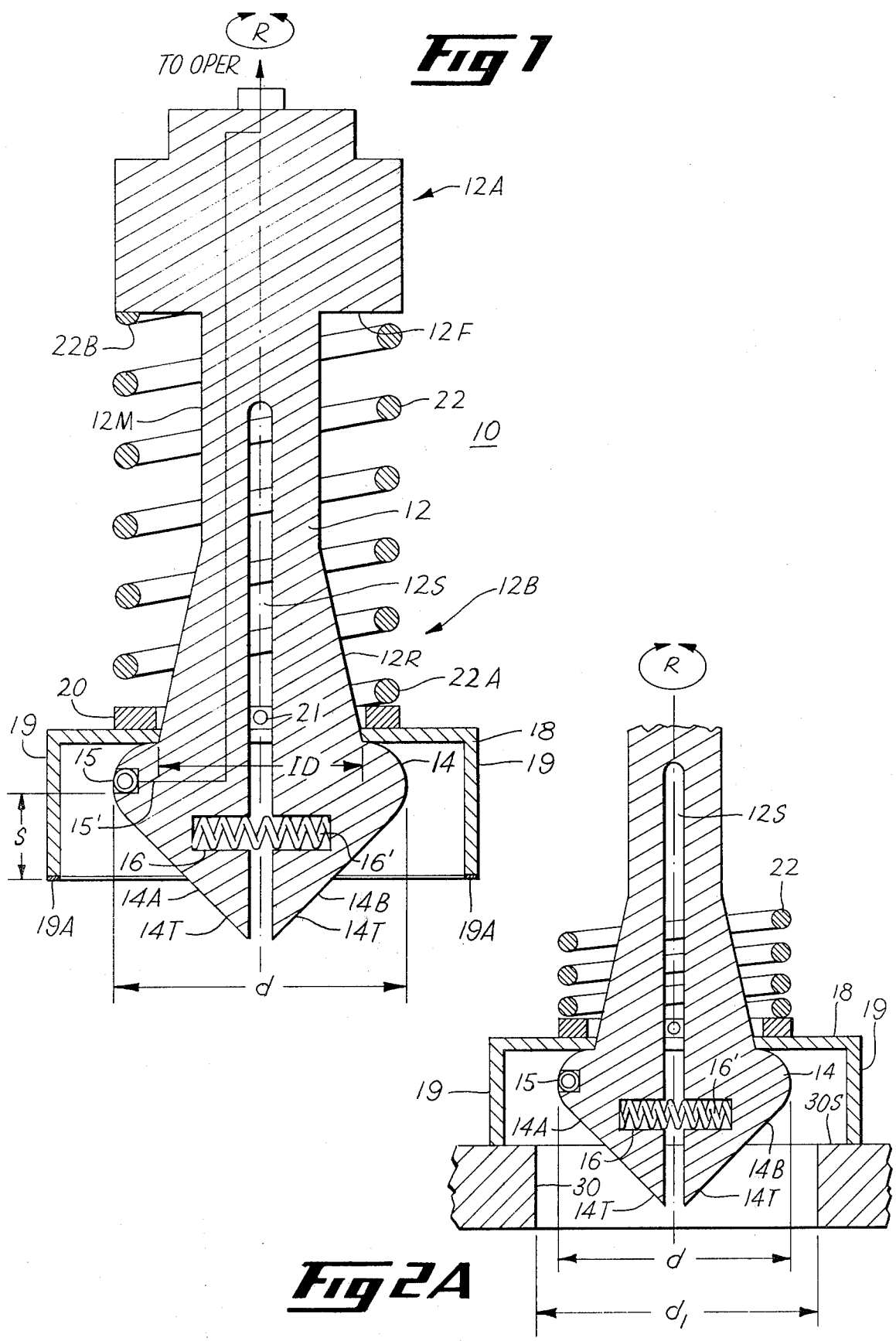

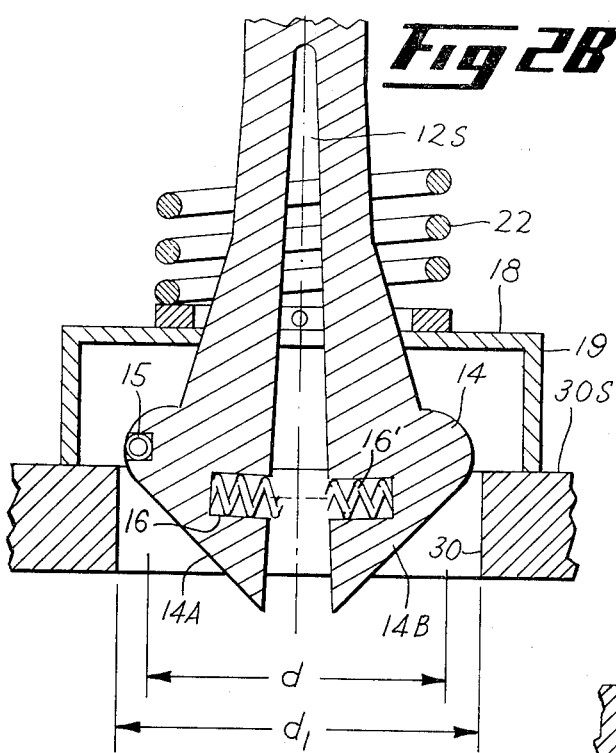
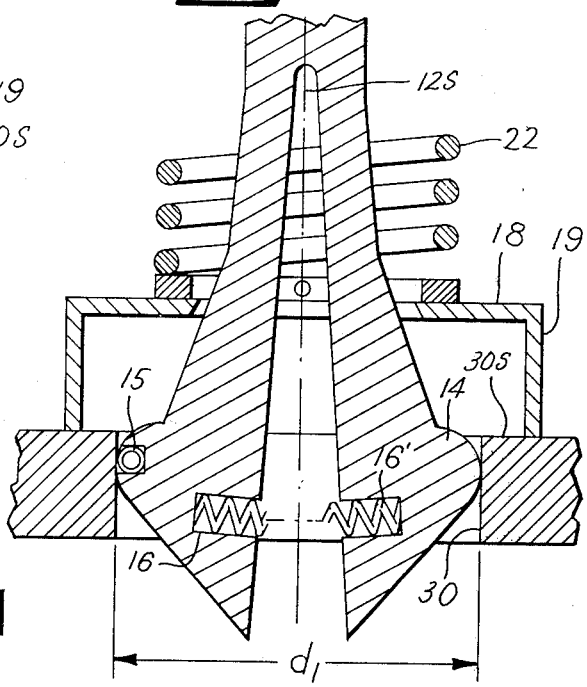
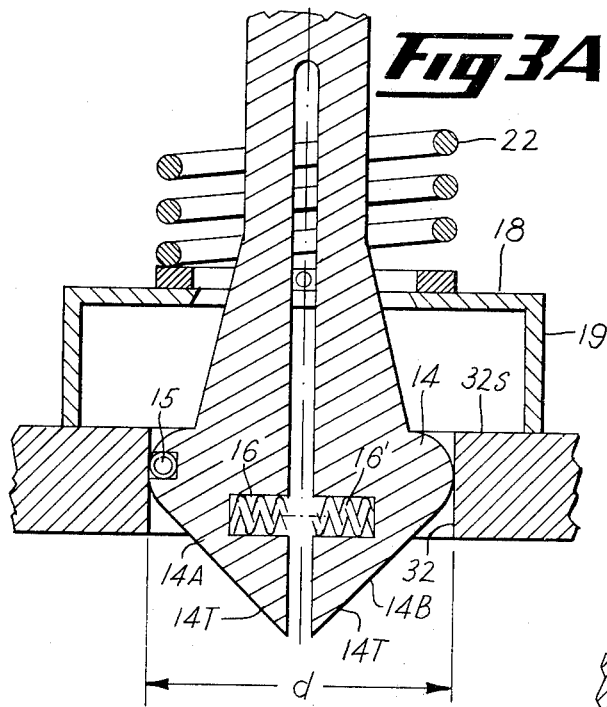
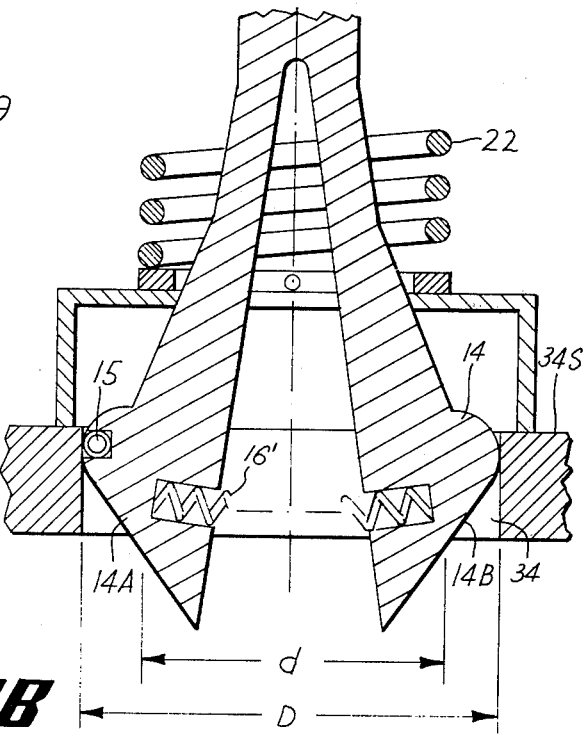

SELF-ADJUSTING INSPECTION APPARATUS

BACKGROUND OF THE INVENTION

The present invention relates to self-adjusting inspection apparatus, and more particularly, to such apparatus for inspecting bolt-holes of various sizes.

Conventional machinery, such as aircraft engines, typically include a plurality of bolt-holes. For many applications, it is necessary to inspect the quality of such bolt-holes. For example, one such inspection technique involves the insertion of an eddy current probe into the bolt-hole which is to be inspected. The eddy current probe includes a probe head having sensor coils located thereon. For accurate eddy current inspection, it is necessary that the sensor coils make firm contact with the bolt-hole interior surface.

One conventional technique for providing the necessary firm contact is to manually wedge the probe head so as to fit the particular bolt-hole which is to be inspected. This wedging technique is often undesirable for industry applications, such as in the manufacture of aircraft engines, where the relatively large variation in bolt-hole sizes renders the technique awkward and time-consuming. More particularly, the variation in bolt-hole size is often such that a probe appropriately wedged to fit one bolt-hole may be too large or too small to fit other bolt-holes. Indeed, in a manual inspection, the probe is generally repeatedly removed and rewedged to fit the other bolt-holes. Further, in view of the need for repeated wedging, this technique is clearly not amenable to an automated inspection system.

Accordingly, it is a general object of this invention to provide improved inspection apparatus.

Another object of the present invention is to provide self-adjusting bolt-hole inspection apparatus.

It is a further object of this invention to provide such inspection apparatus for inspecting bolt-holes of various sizes.

SUMMARY OF THE INVENTION

In carrying out one form of my invention, I provide self-adjusting inspection apparatus for inspecting apertures of a predetermined size range between a minimum inspection dimension and a maximum inspection dimension. Probe shaft means is provided and includes a pair of opposing ends and a midsection. One of the opposing ends is adapted to be coupled to operator means. The other of the opposing ends includes a ramp portion of generally increasing cross section with respect to the cross section of the midsection. Probe head means is coupled to the probe shaft means at the ramp portion remote from the one opposing end. The probe head means is adjustable over the predetermined size range between the minimum dimension and the maximum dimension. The probe head means includes at least two cooperating sections coupled together through first biasing means which normally urges the sections away from each other toward the maximum dimension and which, when urged together, present the minimum dimension. Ramp loading means is slidably positioned around the ramp portion and has an inside dimension such that, as the ramp loading means slides along the ramp portion from the one opposing end of the probe shaft means toward the probe head means, the two cooperating sections are caused to be urged together and the minimum dimension is approached. Second biasing means is positioned around the midsection and coupled to the ramp loading means. The second biasing means normally urges the ramp loading means to a position around the ramp portion at which the cooperating sections are urged together wherein the probe head means presents the minimum dimension. Insertion of the probe head means into the aperture to be inspected compresses the second biasing means and causes the ramp loading means to slide to a position around the ramp portion at which the two sections are urged away from each other wherein the probe head means presents a dimension which corresponds to the inspection dimension of the aperture to be inspected.

BRIEF DESCRIPTION OF THE DRAWINGS

For a better understanding of the invention, reference may be had to the following description, taken in conjunction with the accompanying drawings, wherein:

FIG. 1 is a partially sectioned elevational view showing one form of the self-adjusting inspection apparatus of the present invention.

FIGS. 2A–2C are schematic views, taken as in FIG. 1, showing a portion of the inspection apparatus as employed to inspect a bolt-hole of intermediate diameter.

FIGS. 3A, 3B, are schematic views, taken as in FIGS. 2A–2C, showing the bolt-hole inspection apparatus as employed to inspect a bolt-hole of minimum and maximum diameter, respectively.

DETAILED DESCRIPTION OF THE INVENTION

Referring initially to FIG. 1, one form of self-adjusting probe apparatus of the present invention is generally designated 10. The probe apparatus 10 includes a generally axial shaft 12 having a pair of opposing ends 12A and 12B and a midsection 12M. The midsection 12M may, for example, have a cross section of generally circular and constant diameter. For reasons which will be understood later, the shaft 12 preferably includes an axial slot 12S which extends a predetermined distance therethrough. The shaft 12 may be of any material appropriate for the application involved. For example, for eddy current inspection applications, insulating materials, such as phenolics or plastics, are appropriate.

The end 12A of the shaft 12 is adapted to be connected to signal processing means and/or operator means (not shown in FIG. 1) The signal processing means and operator means may, for example, include conventional rotating equipment for rotating the shaft 12 about its longitudinal axis (see arrow R) while providing for electrical coupling, e.g., slip rings, from the probe apparatus to the signal processing means.

The shaft end 12B includes a ramp portion 12R extending axially from the midsection 12M. The ramp portion 12R is of generally increasing cross section with respect to the cross section of the midsection 12M. Probe head means 14 is coupled to the ramp portion 12R at a position remote from the shaft end 12A. The probe head means 14 may, for example, comprise a pear-shaped structure wherein the end of the probe head means 14 remote from the operator is provided with a tapered edge 14T for facilitating entry into bolt-holes. The probe head means 14 includes at least one conventional eddy current sensor coil 15 located at the largest perimeter of the pear-shaped probe head 14 and adapted for inspecting bolt-holes. Electrical signal line 15' couples the sensor 15 to the appropriate signal processing means (not shown).

The probe head means 14 may include, for example, two cooperating probe sections 14A, 14B, respectively. The cooperating sections 14A, 14B are defined by the shaft slot 12S which passes therethrough and through the midsection 12M. A transverse groove 16 extends into each of the cooperating sections 14A, 14B and a biasing means 16', e.g., a spring, is disposed therein. When the sections 14A, 14B are urged together, the probe head means 14 presents a minimum diameter which is suitable for inspecting bolt-holes of a minimum diameter d. The spring 16 functions to normally bias the cooperating sections 14A, 14B away from each other.

Ramp loading means 18 is provided. As will be appreciated later, the purpose of the ramp loading means 18 is to determine the inspection diameter presented by the cooperating sections 14A, 14B of the probe head means 14. The ramp loading means 18 may, for example, be in the form of a cup which is slidably positioned around the ramp portion 12R and is provided with an inside diameter (ID) which is selected to be smaller than the diameter of the bolt-hole to be inspected. Preferably, the inside diameter (ID) of the cup 18 is slightly smaller than the minimum diameter d. The cup 18 is preferably of a low friction material, e.g., nylon, and includes cup arms 19 which extend generally parallel to the longitudinal axis of the probe apparatus 10. The tips 19A of cup arms 19 are preferably provided with a gripping surface such as high friction rubber.

The cup 18 is normally urged to the position shown in FIG. 1 in which the probe head means 14 presents the minimum diameter d. More particularly, spring retainer means 20, preferably of a low friction material, e.g., nylon, is coupled to the cup 18. The retainer means 20 may also be further coupled to the shaft 12 through a pin 21. The pin 21 rides in the shaft slot 12S so that the spring retainer 20 and cup 18 are axially slidable with respect to the shaft 12. Axial biasing means 22, which may, for example, comprise a spring, is coupled at one end 22A to the retainer 20. The other end 22B of the spring 22 is coupled to a flanged portion 12F which is located at a point further remote from the probe head 14. The spring 22 is selected to provide sufficient force to overcome the force of the transverse spring 16'. Accordingly, under normal operating conditions, the cup 18 is moved along the ramp 12R, resulting in the position shown in FIG. 1 wherein the probe head means 14 presents the minimum diameter d.

Referring now to FIGS. 2A-2C, the use of the self-adjusting inspection apparatus 10 of the present invention in inspecting a bolt-hole of intermediate diameter $d_1$ will be described.

Intermediate diameter $d_1$ represents a bolt-hole 30 having a diameter between a minimum diameter d and a maximum diameter D. More particularly, to inspect the bolt-hole 30, the tip 14T of the probe head means 14 is aligned to the center of the bolt-hole. Typically, rotating motion is imparted to the apparatus 10 by conventional rotating equipment (not shown). Axial motion of the probe head means 14 is initiated into the bolt-hole 30. By the time the cup arms 19 contact the bolt-hole surfaces 30S, the spring retainer 20 and cup 18 function as a rotary bearing surface. As the axial motion of the probe head means 14 continues into the bolt-hole 30, the axial spring 22 begins to compress and the cup 18 moves along the ramp portion 12R from the position shown in FIG. 2A to the position shown in FIG. 2B. During this axial movement, the probe head means 14 diameter begins to increase from the minimum diameter d of FIG. 2A toward the desired intermediate diameter $d_1$. As the axial motion of the probe head means 14 is continued into the bolt-hole 30, the cup 18 continues to move along the ramp 18, resulting in the position shown in FIG. 2C in which the probe head means 14 presents a diameter equal to the intermediate diameter $d_1$. Typically, good inspection can now be accomplished simply by rotating the probe 10 about its longitudinal axis. It is to be appreciated that, once the probe head means 14 obtains the diameter equal to the bolt-hole, the probe head means 14 can be further inserted into the bolt-hole for further inspection.

Thus, as shown in FIG. 2C, the diameter of the probe head means 14 is determined by the bolt-hole diameter $d_1$, thus assuring good contact as required for a quality inspection. After the inspection, when the probe apparatus 10 is axially withdrawn from the bolt-hole 30, the axial spring 22 will again move the cup 18 into the normal position of FIG. 2A, causing the cooperating probe sections 14A, 14B to be urged together. Thus, the probe head means 14 once again presents the minimum diameter d and is ready for the next inspection.

For calibration purposes, it is desirable that the distance S (shown clearly in FIG. 1), representing the axial distance along the cup arms 19 from the bottom of the sensor 15 to the cup arm ends 19A, be carefully selected. More particulary, the distance S should be selected such that the sensor 15 contacts the interior of the bolt-hole at the desired location. Also, the distance S should be selected such that the cup 18 moves the desired distance along the ramp portion 12R whereby the probe apparatus 10 is capable of self adjustment over the desired predetermined range of bolt-hole sizes.

It is to be appreciated that the self-adjusting probe apparatus 10 can inspect bolt-holes of diameters which vary between a predetermined minimum diameter d and a predetermined maximum diameter D.

For example, FIG. 3A shows one form of the probe apparatus 10 as employed to inspect a bolt-hole 32 of the minimum diameter d. The minimum bolt-hole inspection position of FIG. 3A is obtained in a manner similar to the sequence shown in FIGS. 2A-2C. However, in the minimum diameter bolt-hole inspection of FIG. 3A, the probe head sections 14A, 14B are first separated (not shown) as the cup 18 moves along the ramp portion 12R while compressing the spring 22. This separating of the probe sections 14A, 14B is, however, opposed by the further compression of the probe sections 14A, 14B as the tapered edge 14T of the pear-shaped probe head means 14 enters the bolt-hole 32. FIG. 3B depicts, in exaggerated fashion, the situation in which the self-adjusting probe apparatus 10 is employed to inspect a bolt-hole 34 of the maximum diameter D. The probe 10 is again employed as shown in FIGS. 2A-2C. This results in a situation in which the cup 18 has moved sufficiently along the ramp portion 12R so that the probe sections 14A, 14B are urged apart by the spring 16', thereby presenting the maximum diameter D.

Thus, there is provided by the present invention a self-adjusting inspection apparatus for inspecting bolt-holes of diameters which vary between a predetermined minimum diameter d and a predetermined maximum diameter D. The particular range of inspection is determined by the probe configuration. More particularly, the probe head is chosen to present an acceptable, predetermined, minimum diameter d. Then, the length and angle of the ramp portion is chosen to present a maximum available probe head diameter D. Similarly, the axial length of the shaft slot and its width are chosen to provide the desired minimum and maximum probe head diameter.

Although, for purposes of clairty, the present invention has been described in connection with a one-piece shaft structure, it is to be appreciated that the probe need not be integrally formed. In this connection, for certain applications, the probe head may simply be coupled, for example, threaded, to the shaft. Also, the probe shaft may be coupled to the operator means through a conventional connector structure. Indeed, for many applications, such modular construction is desirable for cost and flexibility reasons.

Also, although it is preferable that the shaft include a slot therein for allowing the necessary adjustment and for ensuring that the sensor contacts the bolt-hole interior at a nearly normal inspection angle, such slot is not essential. For example, the probe head may simply comprise a pair of cooperating sections which are pivotally connected at the bottom of the shaft (not shown). Further, although the probe head has been shown as comprising a pear-shaped structure separated into two substantially indentical sections, the cooperating probe sections need not be identical. For example, when used in the conventional rotary eddy current technique, it is only necessary that the sensor make firm contact with the interior of the bolt-hole. Accordingly, the probe section which does not include the sensor functions only as a means for imparting biasing force to the sensor bearing probe section.

The self-adjusting inspection apparatus of the present invention is not limited to the eddy current inspection of bolt-holes. Indeed, the present invention is generally applicable to the inspection of any aperture within a predetermined size range between a minimum inspection dimension and a maximum inspection dimension. In this connection, the apertures to be inspected need not be circular in cross section: the apparatus is well suited for the inspection of irregular cross sections. For example, if desired, the apparatus can be employed to inspect apertures of square or rectangular cross section. For inspecting such noncircular cross section apertures, it is only necessary that the probe head be of a configuration which corresponds to the cross section of the aperture to be inspected. Thus, in the case of a square cross section aperture, the probe head may be box-shaped. Such square and rectangular cross section apertures would not be amenable to rotary inspection but would, of course, be amenable to both static and dynamic inspection.

Also, although the probe apparatus of the present invention has been illustrated in FIGS. 1–3 with a ramp loading means inside diameter (ID) smaller than the minimum diameter d, for certain applications, the ID may be equal to, or greater than the minimum diameter d. However, for such applications, the probe apparatus may not have the wide range of axial inspection capability provided by the probe apparatus of FIGS. 1–3.

While the present invention has been described with reference to specific embodiments thereof, it will be obvious to those skilled in the art that various changes and modifications may be made without departing from the invention in its broader aspects. It is contemplated in the appended claims to cover all such variations and modifications of the invention which come within the true spirit and scope of my invention.

What is claimed as new and desired to be secured by Letters Patent of the United States is:

1. Self-adjusting inspection apparatus for inspecting apertures of a predetermined size range between a minimum inspection dimension and a maximum inspection dimension, which comprises:

probe shaft means having a pair of opposing ends and a midsection with one of said opposing ends adapted to be coupled to operator means and the other of said opposing ends including a ramp portion of generally increasing cross section with respect to the cross section of said midsection;

probe head means coupled to said probe shaft means at said ramp portion remote from said one opposing end, said probe head means being adjustable over the predetermined size range between the minimum dimension and the maximum dimension, said probe head means including at least two cooperating sections coupled together through first biasing means which normally urges said sections away from each other toward the maximum dimension and which when urged together present the minimum dimension;

ramp loading means slidably positioned around said ramp portion and having an inside dimension such that as said ramp loading means slides along said ramp portion from said one opposing end of said shaft means toward said probe head means said two cooperating sections are caused to be urged together and the minimum dimension is approached; and second biasing means positioned around said midsection and coupled to said ramp loading means for normally urging said ramp loading means to a position around said ramp portion at which said two cooperating sections are urged together wherein said probe head means presents the minimum dimension and wherein insertion of said probe head means into said aperture to be inspected compresses said second biasing means and causes said ramp loading means to slide to a position around said ramp portion at which said two sections are urged away from each other wherein said probe head means presents a dimension which corresponds to the inspection dimension of said aperture to be inspected.

2. Self-adjusting inspection apparatus in accordance with claim 1 in which said apertures comprise bolt-holes and in which said minimum and maximum inspection dimensions comprise minimum and maximum inspection diameters, respectively.

3. Self-adjusting inspection apparatus in accordance with claim 2 in which said probe shaft means include an axial slot extending at least partially therethrough.

4. Self-adjusting inspection apparatus in accordance with claim 2 in which said probe head means in pear-shaped with a perimeter corresponding to bolt-hole to be inspected and in which said probe head means includes at least one sensor element disposed at said perimeter.

5. Self-adjusting inspection apparatus in accordance with claim 4 in which said sensor element comprises an eddy current sensor.

6. Self-adjusting inspection apparatus in accordance with claim 2 in which said first and second biasing means comprise first and second springs, respectively.

7. Self-adjusting inspection apparatus in accordance with claim 6 in which said ramp loading means comprises a cup having cup arms which extend toward said probe head means in generally parallel relation to the longitudinal axis of said probe shaft means.

8. Self-adjusting inspection apparatus in accordance with claim 7 in which spring retainer means is disposed between said second spring and said cup for coupling said second spring to said cup.

9. Self-adjusting inspection apparatus in accordance with claim 6 in which said probe shaft means midsection has a generally circular cross section.

10. Self-adjusting inspection apparatus in accordance with claim 5 in which said inside dimension of said ramp loading means is smaller than said minimum inspection dimension.

* * * * *